United States Patent [19]
Uda

[11] Patent Number: 5,635,520
[45] Date of Patent: Jun. 3, 1997

[54] ANTI-ULCER COMPOSITIONS SUITABLE FOR RECTAL ADMINISTRATION

[75] Inventor: Yoshiaki Uda, Yonago, Japan

[73] Assignee: Takeda Chemical Industries, Ltd., Osaka, Japan

[21] Appl. No.: 298,156

[22] Filed: Aug. 30, 1994

[30] Foreign Application Priority Data

Aug. 31, 1993 [JP] Japan .................................. 5-216685
Mar. 30, 1994 [JP] Japan .................................. 6-060972

[51] Int. Cl.$^6$ .................................................. A61K 31/44
[52] U.S. Cl. ...................... 514/338; 514/332; 514/964; 514/966; 424/434; 424/436; 424/487; 424/488; 546/273.7
[58] Field of Search ...................... 514/338, 332, 514/966, 968; 546/271; 424/434, 436, 487, 488

[56] References Cited

U.S. PATENT DOCUMENTS

| | | | |
|---|---|---|---|
| 4,738,974 | 4/1988 | Brandstrom | 514/338 |
| 5,219,870 | 6/1993 | Kim | 514/338 |
| 5,223,515 | 6/1993 | Mikura et al. | 514/322 |

FOREIGN PATENT DOCUMENTS

| | | |
|---|---|---|
| 248634 | 12/1987 | European Pat. Off. . |
| 514008 | 11/1992 | European Pat. Off. . |
| 0514008 | 11/1992 | European Pat. Off. . |

| | | |
|---|---|---|
| 5-213752 | 8/1993 | Japan . |

OTHER PUBLICATIONS

*Glycyrrhizin suppository with improved rectal absorption . . .*, Derwent Publications Ltd., AN92–360693. Jan. 1992.
*Preparations for rectal admin . . .*, Derwent Publications Ltd., AN 82–87046E, 1982

*Primary Examiner*—Deborah D. Carr
*Attorney, Agent, or Firm*—Foley & Lardner

[57] ABSTRACT

The present invention relates to a composition for rectal administration which comprises a benzimidazole compound having antiulcer activity and a salt of $C_{6-20}$ fatty acid, both of which are intermingled with each other in a base for rectal administration.

The composition for rectal administration of the present invention is effective for the treatment of gastrointestinal ulcers, is excellent in the stability of the active ingredient therein and the absorption thereof to thereby insure an early attainment of therapeutically effective blood concentration and permits control of the rate of absorption of the drug. Furthermore, the composition for rectal administration of the present invention swells in the intestinal tract, attaches itself to the mucosa, and releases the active ingredient gradually over a long time to supply the drug at a high concentration and with high efficiency. Therefore, the expected therapeutic efficacy can be obtained at a low dosage level with a minimum of side effect.

9 Claims, No Drawings

ANTI-ULCER COMPOSITIONS SUITABLE FOR RECTAL ADMINISTRATION

FIELD OF THE INVENTION

The present invention relates to a composition for rectal administration comprising a benzimidazole compound having antiulcer activity.

BACKGROUND OF THE INVENTION

Benzimidazole compounds are gathering much attention as therapeutic agents for peptic ulcer and/or prophylactic agents for relapse of ulcer, because they have gastric acid antisecretory and gastric mucosa-protecting activities.

As compositions for rectal administration of such benzimidazole compounds, there has been reported 1) a rectal suppository comprising (i) omeprazole, (ii) a mixture of polyethylene glycols or a mixture of adeps solidus and sodium laurylsulfate and (iii) a water-soluble basic amino acid (U.S. Pat No. 5,219,870), 2) a form of suppositories comprising an omeprazole compound and a neutral fat base (U.S. Pat. No. 4,738,974), and 3) a suppository comprising (i) a 2-[(2-pyridyl)methylsulfinyl]benzimidazole compound having antiulcer activity and (ii) hard fat whose acid value is less than 13 and hydroxy group value is less than 40 (JP-A-5213752), but neither of them is fully satisfactory in the stability of the active ingredient in the composition. A gastrointestinal mucosa-adherent matrix is reported (EP-A-514008), but no rectal dosage composition comprising such mucosa-adherent matrix is known.

OBJECTS OF THE INVENTION

The main object of the present invention is to provide a stabilized composition for rectal administration.

This object as well as other objects and advantages of the present invention will become apparent to those skilled in the art from the following description.

SUMMARY OF THE INVENTION

The inventors of the present invention desired a stabilized composition for rectal administration. As a result of their research, the present inventors took note of the fact that the internal pH of the rectum is consistently in neutral to weakly alkaline condition, viz. in the neighborhood of pH 7.0, and the fact that when a drug is administered into the rectum, it is little metabolized by the so-called first-pass effect but is maintained at effective concentration in the blood for a long time. The inventors accordingly prepared a rectal dosage composition for exploiting the absorbability of the drug from the rectal mucosa and further succeeded in insuring a long-term stability of the drug in such composition by utilizing a salt of a fatty acid of about 6 to 12 carbon atoms as a stabilizer. It was also found that as the result of employment of such a fatty acid salt, not only stabilization of the drug in the composition but also promotion of systemic absorption of the drug can be accomplished. In other words, effective absorption and blood concentration of the drug and, hence, improved efficacy can be expected.

According to the present invention, there is provided:

1) A composition for rectal administration which comprises a benzimidazole compound having antiulcer activity and a salt of a fatty acid of 6 to 20 carbon atoms, both of which are intermingled with each other in a base for rectal administration, 2) The composition according to 1) above, wherein the benzimidazole compound is a 2-[(pyridyl)-methylsulfinyl or -methylthio]benzimidazole derivative or a salt thereof, 3) The composition according to 1) above, wherein the benzimidazole compound is represented by the formula:

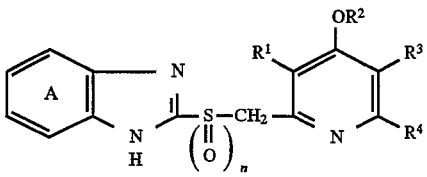

wherein ring A may optionally be substituted, $R^1$, $R^3$ and $R^4$ are, the same or different, hydrogen, an alkyl or alkoxy group, $R^2$ is a hydrocarbon group which may optionally be substituted, and n is 0 or 1, or a salt thereof, 4) The composition according to 1) above, wherein the fatty acid is a saturated fatty acid of 8 to 16 carbon atoms or an unsaturated fatty acid of 12 to 18 carbon atoms, 5) The composition according to 1) above, wherein the salt of the fatty acid of 6 to 20 carbon atoms is an alkali metal or ammonium salt of the fatty acid, 6) The composition according to 5) above, wherein the alkali metal salt is a sodium salt, 7) The composition according to 1) above, wherein the intermingled mixture of the benzimidazole compound and the fatty acid salt is dispersed in a mucosa-adherent matrix, 8) The composition according to 7) above, wherein the mucosa-adherent matrix comprises a polyglycerin fatty acid ester and a viscogenic agent capable of developing viscosity on contact with water, 9) The composition according to 7) above, wherein the viscogenic agent is an acrylic acid polymer or its salt, 10) The composition according to 1) above, wherein the amount of the fatty acid of 6 to 20 carbon atoms is about 0.5 to about 30% by weight based on the composition, 11) The composition according 3) above, wherein $R^1$ is a $C_{1-3}$ alkyl group, $R^2$ is a $C_{1-4}$ alkyl group which may optionally be substituted by halogen or a $C_{1-4}$ alkoxy group, and both of $R^3$ and $R^4$ are hydrogen atoms, 12) The composition according to 1) above, wherein the benzimidazole compound is 2-[2-[3-methyl-4-(2,2,2-trifluoroethoxy)pyridyl]methylsulfinyl]benzimidazole, 13) The composition according to 1) above, wherein the benzimidazole compound is 2-[2-[3-methyl-4-(2,2,3,3-tetrafluoropropoxy)pyridyl]methylthio]benzimidazole, 14) The composition according to 1) above, wherein the benzimidazole compound is 2-[2-(3,5-dimethyl-4-methoxypyridyl)methylsulfinyl]-5-methoxy-1H-benzimidazole, 15) The composition according to 1) above, wherein the benzimidazole compound is sodium salt of 2-[2-[4-(3-methoxypropoxy)-3-methylpyridyl]methylsulfinyl]-1H-benzimidazole, and 16) The composition according to 1) above, wherein the benzimidazole compound is 2-[2-(3,4-dimethoxypyridyl)methylsulfinyl]-5-difluoromethoxy-1H-benzimidazole.

DETAILED DESCRIPTION OF THE INVENTION

The benzimidazole compound having antiulcer activity for use in this invention includes a 2-[(pyridyl)-methylsulfinyl or -methylthio]benzimidazole derivative and a salt thereof, for instance. The preferred are compounds represented by the formula (I):

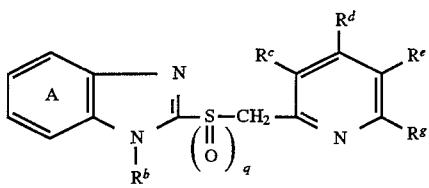

wherein ring A may optionally be substituted; $R^b$ is hydrogen, alkyl, acyl, carbalkoxy, carbamoyl, alkylcarbamoyl, dialkylcarbamoyl or alkylsulfonyl; $R^c$, $R^e$ and $R^g$ are, the same or different, hydrogen, alkyl, alkoxy or alkoxyalkyl; $R^d$ is hydrogen, alkyl or a group of the formula —$OR^f$ in which $R^f$ is a hydrocarbon group which may optionally be substituted, and q is 0 or 1.

These compounds are described in, for example, U.S. Pat. No. 4,045,563, U.S. Pat. No. 4,255,431, U.S. Pat. No. 4,359,465, U.S. Pat. No. 4,472,409, U.S. Pat. No. 4,508,905, EP-A-59 181277, U.S. Pat. No. 4,628,098, U.S. Pat. No. 4,738,975, U.S. Pat. No. 5,045,321, U.S. Pat. No. 4,786,505, U.S. Pat. No. 4,852,230, U.S. Pat. No. 4,769,456, U.S. Pat. No. 5,045,552, EP-A-295603, U.S. Pat. No. 5,312,824, EP-A-166287 and EP-A-519365, etc.

Referring to the above formula (I), the substituent that may optionally be present on ring A includes halogen, alkyl which may be substituted, cycloalkyl which may be substituted, alkenyl which may be substituted, alkoxy which may be substituted, cyano, carboxy, carbalkoxy, carbalkoxyalkyl, carbamoyl, carbamoylalkyl, hydroxy, hydroxyalkyl, acyl, carbamoyloxy, nitro, acyloxy, aryl, aryloxy, alkylthio and alkylsulfinyl, among others.

The respective substituent groups are now specifically described.

The halogen may for example be fluorine, chlorine, bromine or iodine. The preferred are fluorine and chlorine. The most advantageous is fluorine.

The alkyl group for the alkyl which may be substituted includes straight-chain or branched $C_{1-10}$ alkyl groups (e.g. methyl, ethyl, n-propyl, isopropyl, n-butyl, isobutyl, sec-butyl, tert-butyl, n-pentyl, iso-pentyl, neopentyl, hexyl, heptyl, octyl, nonyl and decyl, among others). The preferred are straight-chain or branched $C_{1-6}$ alkyl groups. The still more advantageous are straight-chain or branched $C_{1-3}$ alkyl groups. The substituent on the substituted alkyl includes halogen, nitro, cyano, hydroxy, carboxy, amidino, guanidino and carbamoyl, amino which may be mono- or di-substituted by alkyl, acyl, etc., among others.

The cycloalkyl group for the cycloalkyl which may be substituted includes $C_{3-7}$ cycloalkyl groups. Examples of such cycloalkyl are cyclopropyl, cyclobutyl, cyclopentyl, cyclohexyl and cycloheptyl. Such cycloalkyl groups may each be substituted by, for example, halogen, nitro, cyano, hydroxy, carboxy, amidino, guanidino and carbamoyl, amino which may be mono- or di-substituted by alkyl, acyl, etc., among others.

The alkenyl group for the alkenyl which may be substituted includes straight-chain or branched $C_{2-16}$ alkenyl groups. The preferred alkenyl group includes allyl, vinyl, crotyl, 2-penten-1-yl, 3-penten-1-yl, 2-hexen-1-yl, 3-hexen-1-yl, 2-methyl-2-propen-1-yl and 3-methyl-2-buten-1-yl, among others. The further preferred are straight-chain or branched $C_{2-6}$ alkenyl groups. The still more advantageous are straight-chain or branched $C_{2-4}$ alkenyl groups. Such alkenyl groups may have substituents, such as halogen, nitro, cyano, amidino, guanidino, amino which may be mono- or di-substituted by alkyl, acyl, etc., and so on.

The alkenyl groups mentioned above include isomers (E- and Z-forms) with respect to the double bond.

The alkoxy group for the alkoxy which may be substituted includes $C_{1-10}$ alkoxy groups, among others. As such, the alkoxy group specifically includes methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy, cyclobutoxy, cyclopentoxy, cyclohexyloxy and so on. The preferred are $C_{1-6}$ alkoxy groups. The more advantageous are $C_{1-3}$ alkoxy groups. Such alkoxy groups may be substituted, for example, by halogen, nitro, amidino and guanidio, amino which may be mono- or di-substituted by alkyl, acyl, etc., among others.

The halogen which may occur as a substituent on the above alkyl, cycloalkyl, alkenyl or alkoxy group includes chlorine, bromine, fluorine, iodine, and so on.

The alkyl moiety of the alkylamino which may substitute the above alkyl, cycloalkyl, alkenyl or alkoxy group includes straight-chain or branched $C_{1-6}$ alkyl groups, among preferred examples. The preferred examples are methyl, ethyl, n-propyl, isopropyl, n-butyl, isobutyl, tert-butyl, sec-butyl, n-pentyl, isopentyl, n-hexyl, isohexyl and so on. Among others, particularly are straight-chain or branched $C_{1-4}$ alkyl groups.

The acyl moiety of the acylamino which may substitute the above alkyl, cycloalkyl, alkenyl or alkoxy group includes acyl groups derived from organic carboxylic acids, for instance. The preferred are $C_{1-6}$ alkanoyl groups, such as formyl, acetyl, propionyl, butyryl, isobutyryl, valeryl, isovaleryl, pivaloyl, hexanoyl, etc. Particularly $C_{1-4}$ alkanoyl groups are preferable.

The number of substituents on the above alkyl, cycloalkyl, alkenyl or alkoxy group may range from 1 to 6, preferably 1 to 3.

The substituted alkyl group specifically includes trifluoromethyl, trifluoroethyl, difluoromethyl, trichloromethyl, hydroxymethyl, 1-hydroxyethyl, 2-hydroxyethyl, methoxyethyl, ethoxyethyl, 1-methoxyethyl, 2-methoxyethyl, 2,2-dimethoxyethyl, 2,2-diethoxyethyl and 2-diethylphosphorylethyl, among others. The preferred are difluoromethyl, trifluoromethyl and hydroxymethyl. The more desirable is trifluoromethyl.

The substituted cycloalkyl group specifically includes 2-aminocyclopropan-1-yl, 4-hydroxycyclopentan-1-yl and 2,2-difluorocyclopentan-1-yl, among others.

The substituted alkenyl group specifically includes 2,2-dichlorovinyl, 3-hydroxy-2-propen-1-yl, 2-methoxyvinyl and so on.

The substituted alkoxy group specifically includes difluoromethoxy, trifluoromethoxy, 2,2,2-trifluoroethoxy, 2-methoxyethoxy, 4-chlorobenzyloxy, 2-(3,4-dimethoxyphenyl)ethoxy and so on. The preferred is difluoromethoxy.

The alkoxy moiety of the carbalkoxy group includes $C_{1-7}$ alkoxy groups (e.g. methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, etc.).

The alkoxy moiety of the carbalkoxyalkyl group includes $C_{1-4}$ alkoxy groups (e.g. methoxy, ethoxy, n-propoxy, isopropoxy, n-butoxy, isobutoxy, sec-butoxy, tert-butoxy, etc.), among others. The alkyl moiety includes $C_{1-4}$ groups (e.g. methyl, ethyl, n-propyl, isopropyl, n-butyl, isobutyl, sec-butyl, tert-butyl, etc.), among others. Specifically, carbomethoxymethyl, 2-carbomethoxyethyl, 2-carbomethoxypropyl, carboethoxymethyl, 2-carboethoxyethyl, 2-carbomethoxypropyl, 2-carbomethoxypropyl, carbopropoxymethyl, carbobutoxymethyl, etc. can be mentioned.

The alkyl moiety of the carbamoylalkyl group includes $C_{1-4}$ alkyl groups (e.g. methyl, ethyl, n-propyl, isopropyl, n-butyl, isobutyl, sec-butyl, tert-butyl, etc.).

The alkyl moiety of the hydroxyalkyl group includes $C_{1-7}$ alkyl groups (e.g. methyl, ethyl, n-propyl, isopropyl, n-butyl, isobutyl, sec-butyl, tert-butyl, n-pentyl, isopentyl, neopentyl, hexyl, heptyl, etc.)

The acyl group and the acyl moiety of the acyloxy group respectively include $C_{1-4}$ alkanoyl groups such as formyl, acetyl, propionyl, butyryl, isobutyryl and so on.

The aryl group and the aryl moiety of the aryloxy group respectively include $C_{6-12}$ aryl groups (e.g. phenyl, naphthyl, etc.).

The alkyl moiety of the alkylthio or alkylsulfinyl group includes $C_{1-6}$ alkyl group (e.g. methyl, ethyl, n-propyl, isopropyl, n-butyl, isobutyl, sec-butyl, tert-butyl, n-pentyl, isopentyl, neopentyl, hexyl, etc.)

The number of substituents on substituted ring A is preferably 1 to 4 and, for still better results, 1 to 2. The positions of such substituents on the benzene ring may for example be 4- and 5-positions. The 5-position is preferred.

The preferred is ring A which may optionally be substituted by i) halogen, ii) alkyl group which may be substituted, iii) cycloalkyl group which may be substituted, iv) alkenyl group which may be substituted or v) alkoxy group which may be substituted.

The alkyl group represented by $R^b$, includes $C_{1-5}$ alkyl groups such as methyl, ethyl, n-propyl, isopropyl, n-butyl, isobutyl, sec-butyl, tert-butyl, n-pentyl, isopentyl, neopentyl, etc. The acyl group represented by $R^b$ includes $C_{1-4}$ acyl groups such as $C_{1-4}$ alkanoyl group etc. The carbalkoxy group represented by $R^b$ includes those having $C_{1-4}$ alkoxy groups such as formyl, acetyl, propionyl, butyryl, isobutyryl, etc. The alkylcarbamoyl and dialkylcarbamoyl groups represented by $R^b$ respectively include those having $C_{1-4}$ alkyl moieties such as methyl, ethyl, n-propyl, isopropyl, n-butyl, isobutyl, sec-butyl, tert-butyl, etc. The alkylsulfonyl group represented by $R^b$ includes those having $C_{1-4}$ alkyl moieties such as those mentioned just above. $R^b$ is preferably hydrogen.

The alkyl group represented by $R^c$, $R^e$ or $R^g$ includes straight-chain or branched $C_{1-10}$ alkyl groups (e.g. methyl, ethyl, n-propyl, isopropyl, n-butyl, isobutyl, sec-butyl, tert-butyl, n-pentyl, isopentyl, neopentyl, hexyl, heptyl, octyl, nonyl, decyl, etc.). Among these alkyl groups, straight-chain or branched $C_{1-6}$ alkyl groups to are preferred, and straight-chain or branched $C_{1-3}$ alkyl groups are particularly desirable.

The alkoxy group represented by $R^c$, $R^e$ or $R^g$ includes $C_{1-10}$ alkoxy groups (e.g. methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy, etc.). The preferred are $C_{1-6}$ alkoxy groups. The more desirable are $C_{1-3}$ alkoxy groups.

The alkoxy moiety of the alkoxyalkoxy group represented by $R^c$, $R^e$ or $R^g$ includes $C_{1-4}$ alkoxy groups (e.g. methoxy, ethoxy, n-propoxy, isopropoxy, n-butoxy, isobutoxy, sec-butoxy, tert-butoxy, etc.).

$R^c$ is preferably hydrogen, alkyl or alkoxy.
$R^e$ is preferably hydrogen, alkyl or alkoxy.
$R^g$ is preferably hydrogen.

The alkyl group represented by $R^a$ includes $C_{1-4}$ alkyl groups (e.g. methyl, ethyl, n-propyl, isopropyl, n-butyl, isobutyl, sec-butyl, tert-butyl, etc.).

The hydrocarbon moiety of the hydrocarbon group which may optionally be substituted, represented by $R^f$, is preferably a $C_{1-3}$ hydrocarbon group such as $C_{1-6}$ straight-chain or branched alkyl groups (e.g. methyl, ethyl, propyl, isopropyl, butyl, isobutyl, sec-butyl, pentyl, isopentyl, hexyl, etc.), $C_{2-6}$ alkenyl groups (e.g. vinyl, allyl, 2-butenyl, methylallyl, 3-butenyl, 2-pentenyl, 4-pentenyl, 5-hexenyl, etc.), $C_{2-6}$ alkinyl groups (e.g. ethynyl, propargyl, 2-butin-1-yl, 3-butin-2-yl, 1-pentin-3-yl, 3-pentin-1-yl, 4-pentin-2-yl, 3-hexin-1-yl, etc.), $C_{2-6}$ cycloalkyl groups (e.g. cyclopropyl, cyclobutyl, cyclopentyl, cyclohexyl, etc.), $C_{3-6}$ cycloalkenyl groups (e.g. cyclobutenyl, cyclopentenyl, cyclohexenyl, cyclohexadienyl, etc.), and $C_{7-13}$ aralkyl groups (e.g. benzyl, 1-phenethyl, 2-phenethyl, etc.), and $C_{6-10}$ aryl groups (e.g. phenyl, naphthyl, etc.), and so on. Among others, straight-chain or branched $C_{1-6}$ alkyl groups (e.g. methyl, ethyl, propyl, isopropyl, butyl, isobutyl, sec-butyl, pentyl, isopentyl, hexyl, etc.) are preferred. Particularly, straight-chain or branched $C_{1-4}$ alkyl groups are preferred.

The substituent group of the substituted hydrocarbon group includes, among others, $C_{6-10}$ aryl groups (e.g. phenyl, naphthyl, etc.), amino, $C_{1-6}$ alkylamino (e.g. methylamino, ethylamino, isopropylamino, etc.), di-$C_{1-6}$ alkylamino (e.g. dimethylamino, diethylamino, etc.), azide, nitro, halogen (e.g. fluorine, chlorine, bromine and iodine), hydroxy, $C_{1-4}$ alkoxy (e.g. methoxy, ethoxy, propoxy, butoxy, etc.), $C_{6-10}$ aryloxy (e.g. phenoxy, naphthyloxy, etc.), $C_{1-6}$ alkylthio (e.g. methylthio, ethylthio, propylthio, etc.), $C_{6-10}$ arylthio (e.g. phenylthio, naphthylthio, etc.), cyano, carbamoyl, carboxy, $C_{1-4}$ alkoxycarbonyl (e.g. methoxycarbonyl, ethoxycarbonyl, etc.), $C_{7-11}$ aryloxycarbonyl (e.g. phenoxycarbonyl, 1-naphthyloxycarbonyl, 2-naphthyloxycarbonyl, etc.), carboxy-$C_{1-4}$ alkoxy (e.g. carboxymethoxy, 2-carboxyethoxy, etc.), $C_{1-6}$ alkanoyl (e.g. formyl, acetyl, propionyl, isopropionyl, butyryl, pentanoyl, hexanoyl, etc.), $C_{7-11}$ aroyl (e.g. benzoyl, 1-naphthoyl, 2-naphthoyl, etc.), $C_{6-10}$ arylsulfonyl (e.g. benzenesulfonyl, 1-naphthylsulfonyl, 2-naphthylsulfonyl, etc.), $C_{1-6}$ alkylsulfinyl (e.g. methylsulfinyl, ethylsulfinyl, etc.), $C_{6-10}$ arylsulfinyl (e.g. benzenesulfinyl, 1-naphthylsulfinyl, 2-naphthylsulfinyl, etc.), $C_{1-6}$ alkylsulfonyl (e.g. methylsulfonyl, ethylsulfonyl, etc.), 5- or 6-membered heterocyclic groups having 1 to 4 hetero-atoms (e.g. N, O, S, etc.) (e.g. 2-furyl, 2-thienyl, 4-thiazolyl, 4-imidazolyl, 4-pyridyl, 1,3,4-thiadiazol-2-yl, 1-methyl-5-tetrazolyl, etc.), 5- or 6-membered heterocyclic carbonyl groups having 1 to 4 hetero-atoms (e.g. N, O, S) (e.g. 2-froyl, 2-thenoyl, nicotinyl, isonicotinyl, etc.) and 5- or 6-membered heterocyclic thio groups having 1 to 4 hetero-atoms (e.g. N, O, S, etc.) (e.g. 4-pyridylthio, 2-pyrimidylthio, 1,3,4-thiadiazol-2-ylthio, 1-methyl-5-tetrazolythio, etc.). The heterocyclic thio groups may each form a bicyclic structure with a benzene ring (e.g. 2-benzothiazolylthio, 8-quinolylthio, etc.). The preferred substituents are halogen (e.g. fluorine, chlorine, bromine and iodine), hydroxy, and $C_{1-4}$ alkoxy (e.g. methoxy, ethoxy, propoxy, butoxy, etc.).

The number of such substituents may range from 1 to 5 and is preferably 1 to 3.

$R^d$ is preferably an alkoxy group which may be substituted or an alkoxyalkoxy group which may be substituted. The alkoxy for the alkoxy group which may be substituted includes $C_{1-8}$ alkoxy groups (e.g. methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, etc.). Each of the alkoxy group for the alkoxyalkoxy which may be substituted includes $C_{1-4}$ alkoxy groups (e.g. methoxy, ethoxy, n-propoxy, isopropoxy, n-butoxy, isobutoxy, sec-butoxy, tert-butoxy, etc.). $R^d$ is an optionally halogeno $C_{1-8}$ alkoxy group, preferably an optionally halogeno $C_{1-4}$ alkoxy group, or an optionally halogeno alkoxyalkoxy group. Preferred specific examples of the optionally halogeno alkoxy group are 2,2,2-trifluoroethoxy, 2,2,3,3,3-pentafluoropropoxy, 1-(trifluoromethyl)-2,2,2-trifluoroethoxy, 2,2,3,3-tetrafluoropropoxy, 2,2,3,3,4,4,4-heptafluorobutoxy, 2,2,3,3,4,4,5,5-octafluoropentoxy, methoxy, and the like. The optionally halogeno alkoxyalkoxy group is preferably 3-methoxypropoxy.

The preferred, among the compounds of the formula (I), are (1) compounds wherein ring A is either unsubstituted or substituted by methoxy or trifluoromethyl; $R^b$ is hydrogen; $R^c$ and $R^e$ are, the same or different, hydrogen or methyl; $R^d$ is a $C_{1-5}$ alkoxy which may be fluorinated; $R^g$ is hydrogen; and q is 0 or 1, (2) compounds wherein ring A is unsubstituted or substituted by fluorine, methoxy or trifluoromethyl; $R^b$ is hydrogen; $R^c$ is hydrogen or methoxy; $R^d$ is a $C_{3-8}$ alkoxy group; both of $R^e$ and $R^g$ are hydrogens; and q is 1, and (3) compounds wherein ring A is unsubstituted or substituted by fluorine, methoxy or trifluoromethyl; $R^b$ is hydrogen; $R^c$ is a $C_{1-6}$ alkoxy group; $R^d$ is a $C_{1-8}$ alkoxy group which may be fluorinated; both of $R^e$ and $R^g$ are hydrogens; and q is 1.

The benzimidazole compound having antiulcer activity which is suitable for use in this invention specifically includes compounds represented by the formula (II):

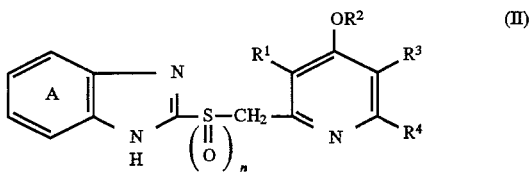

wherein ring A may optionally be substituted; $R^1$, $R^3$ and $R^4$ are, the same or different, hydrogen, an alkyl or alkoxy group; $R^2$ is a hydrocarbon group which may optionally be substituted; n is 0 or 1, and compounds represented by the formula (II'):

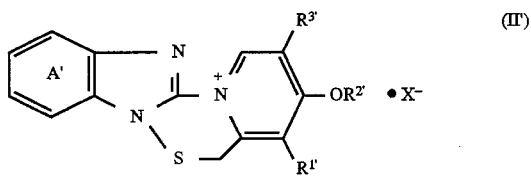

wherein ring A' may optionally be substituted; $R^{1'}$ and $R^{3'}$ are, the same or different, hydrogen, an alkyl or alkoxy group; $R^{2'}$ is a hydrocarbon group which may optionally be substituted; $X^-$ is an anion.

The benzimidazole compound having antiulcer activity which is particularly suited for use in this invention includes the above compounds represented by the formula (II).

Referring to the above formulas (II) and (II'), ring A or ring A' includes those described for ring A in the formula (I).

The alkyl group represented by $R^1$, $R^3$, $R^{1'}$, $R^{3'}$ or $R^4$ includes straight-chain or branched $C_{1-10}$ alkyl groups, such as, methyl, ethyl, n-propyl, isopropyl, n-butyl, isobutyl, sec-butyl, tert-butyl, n-pentyl, isopentyl, neopentyl, hexyl, heptyl, octyl, nonyl, decyl, etc. The preferred are straight-chain or branched $C_{1-6}$ alkyl groups. Particularly desirable are straight-chain or branched $C_{1-3}$ alkyl groups.

The alkoxy group represented by $R^1$, $R^3$, $R^{1'}$, $R^{3'}$ or $R^4$ includes $C_{1-10}$ alkoxy groups, such as methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy, cyclobutoxy, cyclopentoxy, cyclohexyloxy, etc. The preferred are $C_{1-6}$ alkoxy groups. The more desirable are $C_{1-3}$ alkoxy groups.

The hydrocarbon group which may optionally be substituted, represented by $R^2$ or $R^{2'}$, includes those groups mentioned for $R^f$.

$R^1$ or $R^{1'}$ is preferably $C_{1-6}$ alkyl or $C_{1-6}$ alkoxy, more preferably $C_{1-3}$ alkyl.

$R^3$ or $R^{3'}$ is preferably hydrogen or $C_{1-6}$ alky, more preferably hydrogen.

$R^2$ or $R^{2'}$ is preferably $C_{1-6}$ alkyl which may optionally be substituted by halogen, hydroxyl or $C_{1-4}$ alkoxy, more preferably, $C_{1-3}$ alkyl which may optionally be substituted by halogen or $C_{1-4}$ alkoxy.

$R^4$ is preferably hydrogen.

The anion represented by $X^-$ includes halide ions (e.g. iodide ion, bromide ion, chloride ion, etc.), sulfur ion, phosphate ion, nitrate ion, perchlorate ion, tetrafluoroborate ion, methanesulfate ion, p-tolylsulfate ion, benzenesulfate ion, hydroxide ion, organic acid carboxylate ions (e.g. oxalate ion, maleate ion, fumarate ion, succinate ion, citrate ion, lactate ion, trifluoroacetate ion, lactobionate ion, acetate ion, propionate ion, tartrate ion, ethylsuccinate ion, etc.). Preferred, among others, is tetrafluoroborate ion.

The benzimidazole compound having antiulcer activity for use in this invention includes, among specific examples, 2-[2-[3-methyl-4-(2,2,2-trifluoroethoxy)pyridyl]methylsulfinyl]benzimidazole (hereinafter referred to as AG-1749 or lansoprazole), 2-[2-[3-methyl-4-(2,2,3,3-tetrafluoropropoxy)pyridyl]methylthio]benzimidazole (hereinafter referred to as AG-1789), 2-[(2-pyridyl)methylsulfinyl]benzimidazole(thimoprazole), 2-[2-(3,5-dimethyl-4-methoxypyridyl)methylsulfinyl]-5-methoxy-1H-benzimidazole (omeprazole), sodium salt of 2-[2-[4-(3-methoxypropoxy)-3-methylpyridyl]methylsulfinyl]-1H-benzimidazole (E-3810), 2-[2-(3,4-dimethoxypyridyl)methylsulfinyl]-5-difluoromethoxy-1H-benzimidazole (pantoprazole), 4-methyl-3-(2,2,2-trifluoroethoxy)-5H-pyrido[1',2':4,5][1,2,4]thiaziano[2,3-a]benzimidazol-13-ium tetrafluoroborate and so on.

The benzimidazole compound having antiulcer activity for use in this invention can be produced by, inter alia, the processes described in the published literature (JP and European laid-open patents and U.S. patents) or any processes analogous therewith.

The benzimidazole compound having antiulcer activity can be used in the form of a physiologically acceptable salt. The physiologically acceptable salt includes salts with inorganic bases, salts with organic bases, and salts with basic amino acids. Among the inorganic bases mentioned above are alkali metals (e.g. sodium, potassium, etc.) and alkaline earth metals (e.g. calcium, magnesium, etc.). The organic bases may be trimethylamine, triethylamine, pyridine, picoline, N,N-dibenzylethylenediamine, ethanolamine, diethanolamine, trishydroxymethylaminomethane, dicyclohexylamine, etc. The basic amino acids may be arginine, lysine and so on.

These salts can be produced by the per se known production processes, for example the processes described in EP-A-295603 and U.S. Pat. No. 4,738,974 or any processes analogous therewith.

The benzimidazole compound for use in this invention have potent gastric acid antisecretory activity, gastric mucosa-protecting activity and antiulcer activity and, yet, a low toxic potential and, therefore, can find application in the treatment of peptic ulcer in mamalian animals (e.g. mouse, rat, rabbit, dog, cat and man).

The fatty acid for the salt of a fatty acid of 6 to 20 carbon atoms for use in this invention includes a saturated or unsaturated fatty acid of 6 to 20 carbon atoms, such as caproic acid, caprylic acid, perargogic acid, capric acid, lauric acid, myristic acid, palmitic acid, stearic acid, behenic acid, oleic acid, linolic acid, linolenic acid, gadoleic acid, arachidonic acid, linderic acid, laurolenic acid, tsuzuic acid and so on. The preferred are saturated or unsaturated medium carbon number fatty acids (e.g. palmitic acid, caprylic acid, capric acid, lauric acid, myristic acid, oleic acid, linolic acid, linolenic acid, laurolenic acid, etc.). Still more desirable are $C_{8-16}$ saturated fatty acids (e.g. caprylic acid, captic acid, lauric acid, myristic acid, palmitic acid, etc.) or $C_{12-18}$ unsaturated fatty acids (e.g. oleic acid, linolic acid, linoleic acid, etc.). Further, where the mucosa-adherent matrix to be described hereinafter is employed, the $C_{6-20}$ fatty acid salt is preferably a salt which is solid at ordinary temperature. As examples of such salt may be mentioned salts of $C_{10-16}$ saturated fatty acids (e.g. capric acid, lauric acid, myristic acid, palmitic acid, etc.).

The salt of a fatty acid of 6 to 20 carbon atoms is a pharmacologically acceptable salt. Such salt includes salts with metals (e.g. alkali metal salts such as sodium salt, potassium salt, etc., alkaline earth metal salts such as calcium salt, magnesium salt, etc.), ammonium salts, salts with organic amines (e.g. trimethylamine salt, triethylamine salt, ethanolamine salt, diethanolamine salt, trimethylethanolamine salt, etc.). The preferred are alkali metal salts such as sodium salt, potassium salt, etc. and ammonium salt. Among others, sodium salt is more preferred.

The preferred examples of the salt of a $C_{6-20}$ fatty acid are sodium oleate, sodium palmitate, sodium caprate, sodium linolate, sodium laurate and so on.

The proportion of the salt of a $C_{6-20}$ fatty acid is about 0.1 to about 10 moles, preferably about 0.5 to about 2 moles, per mole of the benzimidazole compound having antiulcer activity. If the proportion of the fatty acid salt relative to the benzimidazole compound having antiulcer activity is less than about 0.1 molar equivalent, the benzimidazole compound can be hardly stabilized.

The use of the $C_{6-20}$ fatty acid salt prevents the decomposition and discoloration of the benzimidazole compound having antiulcer activity in the composition for rectal administration of this invention.

The base for rectal administration for use in this invention is not particularly critical in type but can be selected from among the water-soluble bases, oleaginous bases, emulsion bases and ointment bases which are commonly employed in the manufacture of compositions for rectal administration such as suppositories. Among such water-soluble bases are polyethylene glycol (e.g. PEG-400, 1000, 1540, 4000 and 6000, inclusive of their mixtures), glycerin, glycerogelatin, propylene glycol, sorbitol, mannitol, aqueous gel bases such as natural gums (e.g. gum tragacanth, gum acacia, karaya gum, Irish moss, guar gum, xanthan gum, locust bean gum, etc.), cellulose derivatives (e.g. methylcellulose, carboxymethylcellulose, etc.), acrylic polymers (e.g. polyacrylic acid, polymethacrylic acid, etc.), vinyl polymers (e.g. polyvinylpyrrolidone, polyvinyl methyl ether, carboxypolymethylene, etc.), synthetic polysaccharides (e.g. polysucrose, polyglucose, polylactose, etc.), starch, dextrin, pectin, sodium alginate and so on.

Among the oleaginous bases are cacao butter, laurin fat, isocacao, fatty acid glycerides such as Suppocire (Gatefosse, France), Witepsol (Dynamit Nobel, Germany)(e.g. Witepsol W-35, H-5, etc.), Migriol (Dynamit Nobel, Germany), etc., and vegetable oils such as sesame oil, soybean oil, corn oil, cottonseed oil, olive oil and so on.

Among the emulsion bases are systems based on, for example, a) cacao butter formulated with cholesterol and glycerin, with lecithin and water, with Lanette Wax SX (based on cetyl alcohol-stearyl alcohol sulfate ester and containing about 10% of phosphate ester), with cetyl alcohol and sodium lauryl sulfate, or with glycerin monostearate, and b) systems prepared by adding sodium lauryl sulfate, Tween, or the like to fatty acid monoglycerides, monolene (propylene glycol-α-monostearate), wood wax, white Japan wax, stearyl alcohol, cetyl alcohol or the like.

Among the ointment bases are purified lanolin, sodium lauryl sulfate and so on.

Among others, the preferred water-soluble bases are polyethylene glycols, the preferred oleaginous bases are fatty acid mono-, di- or tri-glycerides such as Witepsols and Migriols (Dynamit Nobel, Germany), the preferred emulsion bases are cacao butter-Lanette Wax SX, etc., and the preferred ointment bases are purified lanolin and others.

These bases are used either singly or in combination.

The mucosa-adherent matrix for use in this invention may be any matrix that attaches itself to the intestinal tract and strays there for a sufficiently long time. Such matrix may for example be a mucosa-adherent matrix comprising a polyglycerin fatty acid ester and a substance which develops viscosity in the presence of water (which substance will hereinafter be referred to as a viscogenic agent or viscous agent) or a mucosa-adherent matrix comprising a lipid and a viscous agent. To be specific, such a matrix may for example be a dispersion of the viscous agent in a basal matrix comprising the polyglycerin fatty acid ester or lipid, or a matrix comprising the polyglycerin fatty acid ester or lipid coated with the viscous agent. The preferred matrix is a mucosa-adherent matrix comprising a polyglycerin fatty acid and a viscous agent. Particularly preferred is a dispersion of the viscous agent in a basal matrix comprising a polyglycerin fatty acid ester. The melting point of such a mucosa-adherent matrix may for example be about 30 to about 120° C., preferably about 40° to about 120° C.

Only if it is an ester of a polyglycerin with a fatty acid, the polyglycerin fatty acid ester may be any of the monoester, diester and polyester. The polyglycerin fatty acid ester does not show crystal polymorphism, nor does it interact appreciably with any medicinally active substance. This means that the ester does not appreciably inactivate the medicinally active substance in coexistence but keeps it intact and stable.

Polyglycerin is a polyhydric alcohol having "n(cyclic) to (n+2) (linear or branched) hydroxyl radicals and (n-1) (linear or banched) to n(cyclic) ether bonds" ("Polyglycerin Ester", Sakamoto Yakuhin Kogyo Co., Ltd. (ed.), May 2, 1986, p. 12). The polyglycerin may be linear or branched for use in this invention.

Among others, for example, compounds represented by the formula:

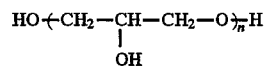

wherein n representing the degree of polymerization is an integer of at least 2, can be mentioned. In the above formula, n is generally an integer of 2 to 50, preferably 2 to 20 and, more preferably 2 to 10. The polyglycerin thus includes diglycerin, triglycerin, tetraglycerin, pentaglycerin, hexaglycerin, heptaglycerin, octaglycerin, nonaglycerin, decaglycerin, pentadecaglycerin, eicosaglycerin, triacontaglycerin and so on. Preferred, among these polyglycerins, are tetraglycerin, hexaglycerin and decaglycerin.

The fatty acid of the polyglycerin fatty acid for use in this invention may for example be a saturated or unsaturated fatty acid of 8 to 40 carbon atoms, preferably 12 to 22 carbon atoms. The preferred fatty acid includes palmitic acid, stearic acid, oleic acid, linolic acid, linolenic acid, myristic acid, lauric acid, ricinoleic acid, caprylic acid, capric acid, behenic acid and so on. Preferred among these fatty acids are stearic acid, oleic acid, lauric acid, linolic acid and behenic acid.

The polyglycerin fatty acid ester includes behenic acid hexa(tetra)glyceride, caprylic acid mono(deca)glyceride, caprylic acid di(tri)glyceride, capric acid di(tri)glyceride, lauric acid mono(tetra)glyceride, lauric acid mono(hexa) glyceride, lauric acid mono(deca)glyceride, oleic acid mono (tetra)glyceride, oleic acid mono(hexa)glyceride, oleic acid mono(deca)glyceride, oleic acid di(tri)glyceride, oleic acid di(tetra)glyceride, oleic acid sesqui(deca)glyceride, oleic acid penta(tetra)glyceride, oleic acid penta(hexa)glyceride, oleic acid deca(deca)glyceride, linolic acid mono(hepta) glyceride, linolic acid di(tri)glyceride, linolic acid di(tetra) glyceride, linolic acid di(hexa)glyceride, stearic acid mono (di)glyceride, stearic acid mono(tetra)glyceride, stearic acid mono(hexa)glyceride, stearic acid mono(deca)glyceride, stearic acid tri(tetra)glyceride, stearic acid tri(hexa) glyceride, stearic acid sesqui(hexa)glyceride, stearic acid penta(tetra)glyceride, stearic acid penta(hexa)glyceride, stearic acid deca(deca)glyceride, palmitic acid mono(tetra) glyceride, palmitic acid mono(hexa)glyceride, palmitic acid mono(deca)glyceride, palmitic acid tri(tetra)glyceride, palmitic acid tri(hexa)glyceride, palmitic acid sesqui(hexa) glyceride, palmitic acid penta(tetra)glyceride, palmitic acid penta(hexa)glyceride, palmitic acid deca(deca)glyceride and so on. The preferred polyglycerin fatty acid ester includes behenic acid hexa(tetra)glyceride (e.g. trade name Poem J-46B, Riken Vitamin K.K.; trade name HB-310, Sakamoto Yakuhin Kogyo), stearic acid penta(tetra)glyceride (e.g. trade name PS-310, Sakamoto Yakuhin Kogyo), stearic acid mono(tetra)glyceride (e.g. trade name MS-310, Sakamoto Yakuhin Kogyo), stearic acid penta(hexa)glyceride (e.g. trade name PS-500, Sakamoto Yakuhin Kogyo), stearic acid sesqui(hexa)glyceride (e.g. trade name SS-500, Sakamoto Yakuhin Kogyo), stearic acid mono(deca)glyceride, etc., and various mixtures thereof.

The above polyglycerin fatty acid esters can be used alone or in combination.

The molecular weight of the polyglycerin fatty acid ester is generally about 200 to about 5000, preferably about 300 to about 2000, and for still better results, about 500 to about 2000. The HLB (hydrophile-lipophile balance) number of the polyglycerin fatty acid is generally 1 to 22, preferably 1 to 15, and more preferably, about 2 to 9. Two or more different kinds of polyglycerin fatty acid may be used in combination to obtain the desired HLB. By adjusting the HLB of polyglycerin fatty acid ester, the release and dissolution kinetics of the drug can be easily controlled.

The proper polyglycerin fatty acid ester can be selected according to the types of active ingredient and viscous substance and matrix form. Generally, an ester which is solid at ordinary temperature (about 15° C.) is employed. The melting point of the polyglycerin fatty acid ester may for example be about 15° to about 80° C., preferably about 30° to about 75° C., and for still better results, about 40° to about 75° C.

Where two or more different kinds of polyglycerin fatty acid ester are used in combination, a liquid polyglycerin fatty acid ester can be included in the combination insofar as the resulting mucosa-adherent matrix will be solid at ordinary temperature.

The lipid for use in this invention is preferably a lipid having a melting point of about 40° to about 120° C., preferably about 40° to about 60° C.

The lipid includes, among others, saturated fatty acids of 14 to 22 carbon atoms (e.g. myristic acid, palmitic acid, stearic acid, behenic acid, etc.) and their salts (e.g. sodium salts, potassium salts, etc.); higher alcohols of 16 to 22 carbon atoms (e.g. cetyl alcohol, stearyl alcohol, etc.); fatty acid glycerin esters which may be the mono-, di- or triglycerides of the above-mentioned fatty acids (e.g. 1-monostearin, 1-monopalmitin, etc.); oils (e.g. castor oil, cottonseed oil, soybean oil, rapeseed oil, beef tallow, etc., and hardened oils thereof etc.); waxes (e.g. beeswax, carnauba wax, sperm wax, etc.); hydrocarbons (e.g. paraffin, microcrystalline wax, etc.); and phospholipids (e.g. hydrogenated lecithin etc.). Preferred among these lipids are oils, waxes, saturated fatty acids of 14 to 20 carbon atoms, higher alcohols of 16 to 20 carbon atoms, hydrocarbons and the like, more preferably, hydrogenated cottonseed oil, hydrogenated castor oil, hydrogenated soybean oil, carnauba wax, stearic acid, stearyl alcohol, microcrystalline wax and so on.

The viscogenic agent capable of developing viscosity on contact with water (viscogenic agent) may be any pharmaceutically acceptable substance that becomes viscous on contact with water and capable of attaching itself to the gastrointestinal mucosa. Preferred is a substance which swells in water and shows a marked increase in viscosity. The viscogenic agent includes synthetic polymers and naturally-occuring viscous substances. Preferred synthetic polymers are those polymers which show viscosities in the range of about 3 to about 50000 cps, preferably about 10 to about 30000 cps and, more preferably, about 15 to about 30000 cps, in 2% aqueous solution, respectively. However, in the case of polymers which show viscosity increases on neutralization, the viscosity of a 0.2% neutralized solution is about 100 to about 500000 cps, preferably about 100 to about 200000 cps, more preferably, about 1500 to about 100000 cps.

The polymer includes acid polymers, preferably polymers having carboxyl or sulfo groups or salts thereof. Among others, polymers having carboxyl groups or salts thereof are more preferred.

Such polymers having carboxyl groups or salts thereof may for example be acrylic acid polymers comprising acrylic acid units (inclusive of copolymers) and salts thereof. Among the salts are salts with monovalent metals such as sodium, potassium, etc. and salts with divalent metals such as magnesium, calcium, etc. The acrylic acid polymers and salts may be those compounds containing about 58–63 weight % of carboxyl groups and having a molecular weight of about $2 \times 10^5$ to about $6 \times 10^6$, preferably about $1 \times 10^6$ to about $5 \times 10^6$. Such acrylic acid polymers or salts include homopolymers of acrylic acid and salts thereof. Such polymers are listed under the heading of carboxyvinyl polymers in the Japanese Ex-Official Drug Formulary (October 1986). Among these polymers are Carbomers [e.g. Carbomer 940, 934, 934P, 940, 941, 1342, etc. (listed in National Formulary XVII), HIVISWAKO (trade name) 103, 104 and 105 (Wako Pure Chemical Industries, Japan), Noveon AA1 (trade name) (The B.F. Goodrich Company), calcium polycarbophil (listed U.S. Pat. No. XXII) and so on.

The naturally-occurring viscous substance includes various mucins, agar, gelatin, pectin, carrageenin, sodium alginate, locust bean gum, xanthane gum, tragacanth gum, gum arabic, chitosan, pullulan, waxy starch, sucralfate, cellulose and its derivatives (e.g. cellulose sulfate etc.), and so on.

The viscogenic agent which is preferred for the purposes of this invention is an acrylic acid polymer and its salt.

These viscogenic agents can be used alone or in combination.

The proportion of the viscogenic agent in the mucosa-adherent matrix may for example be about 0.005 to about 80 weight %, preferably about 0.5 to about 40 weight %, more preferably, about 1 to about 30 weight %. Where the viscogenic agent is dispersed in a basal matrix comprising the polyglycerin fatty acid ester or lipid, its proportion based on the total weight of the matrix is about 0.005 to about 80 weight %, preferably about 0.5 to about 30 weight %, more preferably, about 1 to about 25 weight %. Where a basal matrix comprising the polyglycerin fatty acid ester or lipid is coated with the viscogenic agent, the proportion of the viscogenic agent based on the total weight of the matrix is about 0.005 to about 80 weight %, preferably about 0.5 to about 30 weight %, more preferably, about 1 to about 25 weight %.

Where the mucosa-adherent matrix is a matrix comprising the polyglycerin fatty acid ester and viscogenic agent or a matrix comprising the lipid and viscogenic agent, the proportion of the polyglycerin fatty acid ester or lipid is about 0.001 to about 10000 parts by weight, preferably about 0.001 to about 50 parts by weight, per part by weight of the active ingredient.

The matrix comprising the polyglycerin fatty acid ester may additionally contain a lipid. The lipid for this purpose is a water-insoluble substance which is pharmaceutically acceptable and may regulate the rate of dissolution of the active ingredient. Thus, for example, the lipids mentioned hereinbefore can be employed. Where the lipid and the polyglycerin fatty acid ester are used together, the proportion of the lipid need only be within the range not detracting from the adhesion of the matrix to the mucosa and, as such, may be about 0.01 to about 10.0 parts by weight, preferably about 1 to about 2.0 parts by weight, relative to the active ingredient.

The proportion of the benzimidazole compound having antiulcer activity for use in this invention is about 0.5 to about 5 weight %, preferably about 1 to about 2 weight %, based on the whole composition. The salt of $C_{6-20}$ fatty acid is used in a proportion of about 0.5 to about 30 weight %, preferably about 0.8 to about 10 weight %, and more preferably, about 1 to about 5 weight %, based on the whole composition.

The composition of this invention can be produced by the conventional processes (e.g. manual, melt-forming, cold compression, etc.) which may comprise incorporating the benzimidazole compound having antiulcer activity and $C_{6-20}$ fatty acid salt in a base for rectal administration. An exemplary process comprises admixing the benzimidazole compound and $C_{6-20}$ fatty acid salt evenly into a base for rectal administration and molding the mixture into a suitable form either manually or by means of an extruder. Another alternative process comprises admixing the benzimidazole compound and $C_{6-20}$ fatty acid salt into a base for rectal administration, melting the mixture at low temperature, casting the molten mass into a suitable mold and allowing it to cool.

In this invention, for insuring an enhanced absorption of the drug or controlling the rate of absorption of the drug, nonionic surfactants (e.g. polyoxyethylene cholesterol ether, polyoxyethylene hydrogenated cholesterol ether, polyoxyethylene fatty acid esters, polyoxyethylene higher alcohol ethers, etc.) and/or anionic surfactants (e.g. sodium lauryl sulfate, sodium myristate, sodium stearyl sulfate, etc.) can be used concomitantly. Moreover, for enhanced solubility or stability of the benzimidazole compound, various salts (e.g. salts of organic acids, such as sodium citrate, sodium tartrate, sodium benzoate, etc.) and/or stabilizers (e.g. basic inorganic salts such as magnesium carbonate, calcium carbonate, magnesium hydrogen carbonate, calcium hydrogen carbonate, etc.) can be formulated or added. In addition, small amounts of a preservative, pH control agent, thickener, and/or excipient can be added.

The preservative mentioned above includes parabens, alcohols such as chlorobutanol etc., quaternary ammonium salts such as benzalkonium chloride, benzethonium chloride, cetrimide, etc., sorbic acid, and chlorhexidines, among others. The preferred are parabens.

The pH control agent includes acids, e.g. inorganic acids such as hydrochloric acid, boric acid, phosphoric acid, carbonic acid, bicarbonic acid, etc., organic acids such as mono- or polycarboxylic acids, and amino acids, and bases, e.g. alkali metal hydroxides such as sodium hydroxide, potassium hydroxide, etc., sodium hydrogen carbonate, sodium carbonate and other alkali metal salts. The buffer includes Sörensen buffer [Ergb. Physiol. 32, 393 (1912)], Clark-Lubs buffer [J. Bact. 2, (1), 109, 191 (1917)], MacIlvaine buffer [J. Biol. Chem. 49, 183 (1921)], Michaelis buffer [Die Wasserstoffionen-konzentration, p.186 (1914)] and Kolthoff buffer [Biochem. Z. 179, 410 (1926)], among others.

The thickener includes natural gums such as xanthan gum, locust bean gum, etc., cellulose derivatives such as methylcellulose, carboxymethylcellulose, etc., acrylic polymers such as polyacrylic acid etc., and vinyl polymers such as polyvinylpyrrolidone, polyvinyl alcohol, etc., among others.

Where a mucosa-adherent matrix is employed, the composition for rectal administration of this invention can be manufactured by dispersing the benzimidazole compound having antiulcer activity and the $C_{6-20}$ fatty acid salt in such a mucosa-adherent matrix and molding the dispersion together with a base for rectal administration into a suitable dosage form in a per se known manner. Thus, for example, the benzimidazole compound having antiulcer activity and $C_{6-20}$ fatty acid salt may be dispersed (1) in a mucosa-adherent matrix comprising a dispersion of the viscogenic agent in a basal matrix comprising the polyglycerin fatty acid ester or lipid or (2) in a viscogenic agent-coated basal matrix comprising the polyglycerin fatty acid ester or lipid and the resultant dispersion is incorporated in a suppository base.

The preferred is the first-mentioned procedure, which comprises the benzimidazole compound having anti-ulcer activity and $C_{6-20}$ fatty acid salt is dispersed in a mucosa-adherent matrix comprising a dispersion of the viccous agent in a basal matrix comprising the polyglycerin fatty acid ester or lipid and the resultant dispersion is incorporated in a base for rectal administration.

The mucosa-adherent matrix comprising the benzimidazole compound having antiulcer activity a $C_{6-20}$ fatty acid salt and a dispersion of the viscogenic agent in a basal matrix comprising the polyglycerin fatty acid ester or lipid can be provided by the per se known method. An exemplary process comprises melting the polyglycerin fatty acid ester or lipid under heating at a temperature not below its melting point, adding the viscogenic agent, the benzimidazole compound having antiulcer activity and $C_{6-20}$ fatty acid salt thereto either simultaneously or serially and cooling the resulting dispersion. The heating temperature is about 40° to about 150° C., preferably about 40° to about 95° C., and more preferably, about 45° to about 90° C. The dispersion procedure can be provided conventional method. The procedure mentioned above can be carried out using granulating machines of the conventional type, for instance. For example, spray chilling or the like method is preferably employed to provide a spherical dosage form (e.g. fine granules). Such spray chilling can, for example, be effected by dripping a dispersion of the viscogenic agent, the benzimidazole compound having antiulcer activity and $C_{6-20}$ fatty acid salt in a molten polyglycerin fatty acid ester or lipid on a high-speed rotary disk revolving at 10–6000 rpm, preferably 900–6000 rpm and more preferably 1000–3000 rpm at a constant dripping rate. The rotary disk may for example be a flat, smooth disk, e.g. made of aluminum, which may be 5–100 cm, preferably 10–20 cm, in diameter, for instance. The dripping speed of the molten dispersion can be selected according to the desired particle size but is generally about 2 to about 200 g/min, preferably about 5 to about 100 g/min. The granules thus obtained are close to true spheres and, therefore, can be uniformly coated in the subsequent coating step.

As an alternative procedure, the polyglycerin fatty acid ester or lipid, the viscogenic agent, the benzimidazole compound and the $C_{6-20}$ fatty acid salt can be dispersed, for example by kneading, and granulated. The solvent that can be used for this purpose includes the common solvents (e.g. methanol, acetonitrile, chloroform, etc.).

Furthermore, a mucosa-adherent matrix containing a dispersion of the benzimidazole compound and $C_{6-20}$ fatty acid salt can be prepared by a melt-granulation process. The melt-granulation process includes a process which comprises melting the polyglycerin fatty acid ester or lipid at a temperature near its melting point, for example at a temperature ranging from the melting point to a temperature about 5° C. below the melting point, subjecting the resultant melt to granulation, for example by spray chilling, to prepare fine granules, and fluidizing the resultant granules together with the viscogenic agent, the benzimidazole compound and the $C_{6-20}$ fatty acid in a current of air under mild heating to provide a medicated mucosa-adherent matrix.

The viscogenic agent-coated mucosa-adherent basal matrix comprising the polyglycerin fatty acid ester or lipid may be a basal matrix coated with the viscogenic agent as such but is preferably one coated with a coating composition containing the viscogenic agent as an essential component. Such coating composition may contain, in addition to the viscogenic agent, at least one component selected from the group consisting of the polyglycerin fatty acid esters and lipids mentioned hereinbefore and water-insoluble polymers. In this case, when a viscogenic agent which is poorly compatible or incompatible with the material constituting the basal matrix is selectively used, the basal matrix can be coated with a film in which the viscous substance has been dispersed. The coating agent may contain various additives.

The water-insoluble polymers mentioned above can be selected from among various polymers such as hydroxypropylmethylcellulose phthalate (JP XI), hydroxypropylmethylcellulose acetate succinate (Shin-Etsu Chemical Industry), carboxymethylethylcellulose (Freund Industrial Co.; CMEC, Ex-Official Drug Formulary 1986), cellulose acetate trimellitate (Eastman), cellulose acetate phthalate (JP XI), ethylcellulose (Asahi Kasei, FMC), aminoalkyl methacrylate copolymer (Röhm Pharma, Eudragit E100), aminoalkyl methacrylate copolymer (Röhm Pharma, Eudragit RS, RN 100L, RSPML, RN100 and RSPM), methacrylic acid copolymer L (Röhm Pharma, Eudragit L100), methacrylic acid copolymer L-D (Röhm Pharma, Eudragit L-30-D-55), methacrylic acid copolymer S (Röhm Pharma, Eudragit S-100), polyvinyl acetate phthalate (Colorcon), Eudragit NE30-D (Röhm Pharma) and so on. These water-insoluble polymers can be used alone or in combination.

The amount of the viscogenic agent in the coating composition containing such viscogenic agent is about 0.005 to about 90 weight %, preferably about 0.05 to about 80 weight %, more preferably about 0.05 to about 30 weight % and for still better results, about 1 to about 10 weight %, based on the total nonvolatile matter of the composition.

Where the coating composition contains at least one member selected from the group consisting of the polyglycerin fatty acid ester, lipid and water-insoluble polymer in combination with the viscogenic agent, the proportion of the viscogenic agent based on the total nonvolatile of the composition is about 0.005 to about 90 weight %, preferably about 0.5 to about 30 weight % and, for still better results, about 3 to about 20 weight %.

Furthermore, the coating composition may contain two or more different members selected from the group consisting of the polyglycerin fatty acid ester, lipid and water-insoluble polymer. In this case, based on each part by weight of the total amount of polyglycerin fatty acid ester and/or lipid, the proportion of the other component or components can be about 0.0001 to about 1000 parts by weight, preferably about 0.01 to about 100 parts by weight, and for still better results, about 0.01 to about 10 parts by weight.

The amount of the coating composition relative to the basal matrix can be selected according to the type of basal matrix and the desired adhesiveness of the matrix to the mucosa. The amount of the coating composition relative to the basal matrix may for example be about 0.1 to about 30 weight %, preferably about 0.5 to about 10 weight % for tablets, about 0.1 to about 50 weight %, preferably about 1 to about 20 weight %, for pills and granules, and about 0.1 to about 100 weight %, preferably about 1 to about 50 weight %, for fine granules.

In the coating step, various additives, which are conventionally used, can be added to the coating composition. As an alternative, the coating composition and the additives may be added independently of each other. The amount of such additives relative to the nonvolatile matter of the coating composition may for example be about 0.1 to about 70 weight %, preferably about 1 to about 50 weight % and for still better results, about 20 to about 50 weight %.

The coating operation can be carried out by the per se known procedures, such as pan coating process, fluidized coating process, tumbler process and so on. Where the coating composition is a solution or dispersion in water or an organic solvent, the spray coating process can also be adopted. The proportion of the water or organic solvent may for example be about 25–99 weight %. The kind of organic solvent that can be used is virtually not restricted. Thus, for example, alcohols such as methanol, ethanol, isopropyl alcohol, etc., ketones such as acetone, and halogenated hydrocarbons such as chloroform, dichloromethane, trichloroethane, etc. can be employed.

Where the polyglycerin fatty acid ester and/or lipid is used in the coating composition, a coated matrix can be manufactured by a process which comprises melting the polyglycerin fatty acid ester and/or lipid, if necessary together with the additives, emulsifying the melt with water, spraying the resultant emulsion against the surface of the basal matrix and drying the spray-coated matrix. An alternative process may comprise preheating the basal matrix with hot air in a coating pan, adding the coating composition and allowing the composition to spread on the surface of the matrix to provide a coated matrix.

Coating of the basal matrix can be carried out at a temperature of, generally, about 25° to about 60° C. and, preferably, about 25° to about 40° C.

The coating time can be selected in consideration of the coating procedure, the characteristics and amount of the coating composition used and the characteristics of the basal matrix, among other factors.

If necessary, the mucosa-adherent matrix may be further coated with a conventional water-soluble coating material only if the adhesiveness of the matrix to the mucosa is not adversely affected.

A variety of per se known methods can be used for incorporating the mucosa-adherent matrix containing the benzimidazole compound and $C_{6-20}$ fatty acid salt in a base for rectal administration. An exemplary method comprises melting a base for rectal administration at a temperature of, e.g., about 30° to about 70° C. and dispersing the matrix in the molten base. The dispersion temperature is not particularly restricted but need only be such that the benzimidazole compound will not be dissipated from the matrix during the procedure. The dispersion temperature is generally somewhere between the melting point of the mucosa-adherent matrix and that of the base for rectal administration, namely about 20° to about 90° C. and preferably about 30° to about 60° C. The concentration of the benzimidazole compound in the base for rectal administration is generally about 0.001 to about 99 weight % and preferably about 0.1 to about 80 weight %.

An organic acid may be added, in an appropriate amount, to the mucosa-adherent matrix for promoting the absorption of the active ingredient. The organic acid that can be used includes tartaric acid, citric acid, succinic acid and ascorbic acid, among others.

Furthermore, the conventional additives suitable for the manufacture of solid pharmaceutical dosage forms (e.g. fine granules, granules, etc.) can be added to the matrix according to this invention. Among such additives are various excipients such as lactose, corn starch, talc, crystalline cellulose (e.g. Avicel), powdered sucrose, magnesium stearate, mannitol, light silicic anhydride, magnesium carbonate, calcium carbonate, L-cysteine, etc.; binders such as starch, sucrose, gelatin, gum Arabic powder, methylcellulose, carboxymethylcellulose, carboxymethylcellulose sodium, hydroxypropylcellulose, hydroxypropylmethylcellulose, polyvinylpyrrotidone, pullulan, dextrin, etc.; disintegrators such as carboxymethylcellulose calcium, low-substitution-degree hydroxypropylcellulose, croscarmellose sodium, etc.; surfactants inclusive of anionic surfactants such as sodium alkylsulfate, etc. and nonionic surfactants such as polyoxyethylene sorbitan fatty acid ester, polyoxyethylene fatty acid ester, polyoxyethylene castor oil derivative, etc.; antacids or mucosal protectants such as magnesium hydroxide, magnesium oxide, aluminum oxide, aluminum sulfate, magnesium aluminometasilicate, magnesium aluminosilicate, sucralfate, etc.; coloring agents, corrigents, adsorbents, preservatives, wetting agents, antistatic agents, disintegration retardants, and so on. These additives can be added in amounts not affecting the adhesiveness of the matrix to the mucosa.

The mucosa-adherent matrix according to this invention can be processed into various dosage forms such as powders, granules and so on. The grain size of such mucosa-adherent matrix is not particularly restricted but can be selected according to the required adhesiveness to the gastrointestinal mucosa, the expected release kinetics, i.e. timing and rate, of the active ingredient from the matrix. For example, the composition may comprise not less than about 75 weight % of particles in the range of 10–1000 µm, not more than about 5 weight % of particles over 1000 µm, and not more than about 10 weight % of particles in the range of 10 µm in diameter. The release kinetics of the active ingredient from the mucosa-adherent matrix can be controlled by a suitable procedure such as coating.

The amount of the mucosa-adherent matrix in the composition for rectal administration can be selected according to the intended dosage of the active ingredient. Thus, it may for example be about 0.1 to about 90 weight % and preferably about 1 to about 80 weight %.

A variety of per se known methods can be used for shaping the mucosa-adherent matrix-containing base for rectal administration. For example, it can be molded manually or by means of an extruder or the like, or cast in a suitable mold and cooled.

The composition for rectal administration of this invention is very safe to man and animals.

The dosage of the composition for rectal administration of this invention can be an effective dose of the benzimidazole compound. For example, the dosage for adults (body weight 50 kg), in terms of the benzimidazole compound, may be about 1 to about 200 mg/day, preferably about 5 to about 100 mg/day, and for still better results, about 10 to about 60 mg/day.

The dosage form for the composition of this invention includes solid suppositories (e.g. water-soluble solid suppository, oleagenous solid suppository, etc.), semi-solid suppositories (e.g. ointment suppository, gel or jelly suppository, etc.) and liquids or suspensions (rectal capsule, clysma or enema, etc.), among others. The liquid composition may be filled into soft capsule shells to provide encapsulated suppositories.

The composition for rectal administration of this invention is rectally administered to warm-blooded animals such as man, dog and rat, etc.. The method for administration may be conventional, for example, inserting one solid suppository directly into the anus or inserting a semi-solid, foam or solution dosage form with the aid of an inserter. In this manner, a therapeutically effective dose of the active compound can be administered for absorption through the rectal mucosa of the host for the treatment or therapy of diseases (e.g. ulcer) of the digestive tract (e.g. stomach and intestines).

The composition for rectal administration of the present invention is effective for the treatment of gastrointestinal ulcers, is excellent in the stability of the active ingredient therein and the absorption thereof, to thereby insure an early attainment of therapeutically effective blood concentration, and permits control of the rate of absorption of the drug. Furthermore, the composition for rectal administration of the present invention swells in the gastrointestinal canal, attaches itself to the mucosa, and releases the active ingredient gradually over a long time to supply the drug at a high concentration and with high efficiency. Therefore, the expected therapeutic efficacy can be obtained at a low dosage level with a minimum of side effect.

The following experiment examples and working examples are intended to illustrate the present invention in further detail.

EXPERIMENT EXAMPLE 1

Using PEG-4000 (Wako Pure Chemical Industries, Japan) or Witepsol W-35 (Dynamit Novel, Germany) as a base for rectal administration, the stability of lansoprazole in the composition was compared between the inclusion of sodium oleate and the exclusion of sodium oleate.

PEG-4000 and Witepsol W-35 were provided in the amounts indicated in Table 1. After each of them was melted by warming at 60° C., 20 mg of lansoprazole and a specified amount [See Table 1] of sodium oleate were admixed with the base to prepare a composition. Each composition was stored at room temperature (25° C.) and the change in color was evaluated by comparing it with the composition prior to storage. The results are shown in Table 1.

TABLE 1

| Base (mg) | Fatty acid salt (mg) | After 1 week | After 1 month |
| --- | --- | --- | --- |
| Control | | | |
| PEG-4000 (980) | — | Yellow brown | Brown |
| Witepsol W-35 (980) | — | Brown | Brown |
| Invention | | | |
| PEG-4000 (960) | Sodium oleate (20) | No change | No change |
| Witepsol W-35 (960) | Sodium oleate (20) | No change | No change |

It is apparent from Table 1 that sodium oleate stabilized lansoprazole.

EXPERIMENTAL EXAMPLE 2

Using different fatty acid salts, the stability of lansoprazole in compositions for rectal administration was evaluated by the same procedure as Experiment Example 1. EPG-4000 or Witepsol W-35 was used as the base and sodium oleate, sodium palmitate or sodium caprate was used as the fatty acid salt, each in the amount indicated in Table 2. In this stability test, the test compositions were stored at a temperature of 40° C. and a relative humidity of 75%. The results are shown in Table 2.

TABLE 2

| Base (mg) | Fatty acid salt (mg) | After 1 week | After 1 month |
| --- | --- | --- | --- |
| Control | | | |
| PEG-4000 (980) | — | Yellow brown | Brown |
| Witepsol W-35 (980) | — | Brown | Brown |
| Invention | | | |
| PEG-4000 (960) | Sodium oleate (20) | No change | No change |
| PEG-4000 (960) | Sodium palmitate (20) | No change | No change |
| PEG-4000 (960) | Sodium caprate (20) | No change | No change |
| Witepsol W-35 (960) | Sodium oleate (20) | No change | No change |
| Witepsol W-35 (960) | Sodium palmitate (20) | No change | No change |
| Witepsol W-35 (960) | Sodium caprate (20) | No change | No change |

It is apparent from Table 2 that any of sodium oleate, sodium palmitate and sodium caprate contributed a great deal to the stability of the active drug.

EXAMPLE 1

A base for rectal administration (9.6 g) prepared by blending PEG-400, PEG-1000 and PEG-6000 in a ratio of 0.1:1.4:1.5 (by weight; the same applies hereafter) was evenly melted at 60° C. Then, 0.2 g of lansoprazole and 0.2 g of sodium oleate were added to the base and uniformly dispersed. The resultant dispersion was filled in 2.0 g portions into plastic rectal suppository containers and the filled containers were cooled gradually to provide rectal suppositories.

EXAMPLE 2

As the base for rectal administration, Witepsol W-35 (Dynamit Noble)(9.6 g) was warmed to melt at 60° C. and 0.2 g of lansoprazole and 0.2 g of sodium oleate were added to the base and evenly dispersed. The dispersion was filled in 2.0 g portions into plastic suppository containers and the filled containers were cooled gradually to provide rectal suppositories.

EXAMPLE 3

A base (9.6 g) prepared by blending PEG-1000 and PEG-6000 in a ratio of 1.5:1.0 was evenly melted at 60° C. and 0.2 g of AG-1789 and 0.2 g of sodium oleate were uniformly dispersed in the base. The dispersion was filled in 2.0 g portions into plastic suppository containers and the filled containers were cooled gradually to provide rectal suppositories.

EXAMPLE 4

As the base, Witepsol W-35 (Dynamit Nobel) (9.6 g) was evenly melted at 60° C. and 0.2 g of AG-1789 and 0.2 g of sodium oleate were uniformly dispersed in the base. The dispersion was filled in 2.0 g portions into plastic suppository containers and the filled containers were gradually cooled to provide rectal suppositories.

EXAMPLE 5

As the base, Witepsol H-5 (Dynamit Nobel)(9.6 g) was evenly melted at 60° C. as base and 0.2 g of lansoprazole and 0.2 g of sodium palmitate were uniformly dispersed in the base. This dispersion was filled in 2.0 g portions into rectal suppository containers and the filled containers were gradually cooled to provide rectal suppositories.

EXAMPLE 6

A base (9.6 g) prepared by blending PEG-1000 and PEG-6000 in a ratio of 1.5:1 was evenly melted at 60° C. and 0.2 g of lansoprazole and 0.2 g of sodium caprate were uniformly dispersed in the base. The dispersion was filled in 2.0 g portions into plastic rectal suppository containers and the filled containers were gradually cooled to provide rectal suppositories.

EXAMPLE 7

A base (9.6 g) prepared by blending PEG-400, PEG-1000 and PEG-6000 in a ratio of 0.1:1.4:1.5 was evenly melted at 60 ° C and 0.2 g of sodium salt of 2-[2-[4-(3-methoxypropoxy)-3-methylpyridyl]methylsulfinyl]-1H-benzimidazole and 0.2 g of sodium oleate were uniformly dispersed in the base. This dispersion was filled in 2.0 g portions into plastic rectal suppository containers and the filled containers were gradually cooled to provide rectal suppositories.

EXAMPLE 8

A base (9.6 g) was prepared by blending PEG-400, PEG-1000 and PEG-6000 in a ratio of 0.1:1.4:1.5 was evenly melted at 60° C and 0.2 g of 2-[2-(3,5-dimethyl-4-methoxypyridyl)methylsulfinyl]-5-methoxy-1H-benzimidazole and 0.2 g of sodium oleate were uniformly dispersed in the base. This dispersion was filled in 2.0 g portions into plastic rectal suppository containers and the filled containers were gradually cooled to provide rectal suppositories.

EXAMPLE 9

As the base, Witepsol W-35 (Dynamit Nobel)(9.6 g) was warmed to melt at 60° C. and 0.2 g of pantoprazole and 0.2 g of sodium oleate were uniformly dispersed. This composition was filled in 2.0 g portions into plastic rectal suppository containers and the filled suppositories were gradually cooled to provide rectal suppositories.

Detection: A UV spectrophotometer (exciting wavelength 285 nm)

Column temperature: Room temperature

TABLE 3

| Route of administration | Plasma concentration of lansoprazol, µg/ml | | | | | | | | |
|---|---|---|---|---|---|---|---|---|---|
| | (hr) | | | | | | | | |
| | 0.08 | 0.17 | 0.25 | 0.5 | 1.0 | 2.0 | 4.0 | 8.0 | $AUC_0^{8*}$ |
| Intravenous | 6.96 | 5.39 | 4.83 | 3.28 | 0.91 | 0.07 | 0.005 | 0.002 | 3.86 |
| Rectal Water-soluble base | 0.16 | 0.24 | 0.31 | 0.42 | 0.33 | 0.11 | 0.06 | 0.03 | 0.89 |
| Oleaginous base | 0.09 | 0.14 | 0.21 | 0.31 | 0.36 | 0.18 | 0.09 | 0.05 | 1.08 |

*Area under the plasma concentration-time curve, µg · hr/ml.

EXAMPLE 10

In the same manner as Experiment Example 1 mentioned above, 960 mg of PEG-6000, 20 mg of lansoprazole and 20 mg of sodium oleate were evenly melted and dispersed. The resulting dispersion was filled in 200 mg portions into metallic rectal suppository containers for rats and cooled to provide composition for rectal administration for rats. In addition, using 960 mg of Witepsol W-35 (Dynamit Nobel), 20 mg of lansoprazole and 20 mg of sodium oleate, composition for rectal administration for rats in otherwise the same manner as above.

Male SD rats weighing 250–280 g (Japan Clea) were provided. The animals were allowed food and water ad libitum and, then, fasted for about 16 hours (water was available ad libitum). Using the rats fasted for about 16 hours, the composition for rectal administration prepared above were inserted into the anus and, to prevent expulsion of the drug, the perianal skin was clipped.

For control purposes, 80 mg of lansoprazole, 1.5 ml of PEG-400 and 9.5 ml of 0.5% aqueous solution of sodium hydrogen carbonate were admixed to prepare an injectable solution. This solution was injected, in a volume of 0.25 ml, into the femoral vein of each rat (intravenous dosing).

At 0.08, 0.17, 0.25, 0.5, 1.0, 2.0, 4.0 and 8.0 hours after administration, the blood was drawn from the caudal vein of rats using a blood sampling tube containing a small amount of heparin. Each blood sample was centrifuged (3000 rpm, 10 min.) to separate the plasma (0.1 ml) and lansoprazole in each plasma sample was assayed. The assay method was as follows. To 0.1 ml of plasma were added 0.5 ml of 0.5% aqueous solution of sodium hydrogen carbonate and 3 ml of chloroform and the mixture was shaken vigorously for about 5 minutes and centrifuged at 2500 rpm for about 5 minutes. The under layer (chloroform layer), 2 ml, was taken and the solvent chloform was evaporated off by blasting with nitrogen gas. The residue was redissolved in 0.2 ml of HPLC mobile phase and subjected to HPLC analysis (injection amount 50 µl) under the following conditions. The results are shown in Table 3.

HPLC Conditions

Column: YMC A-303 (5 µm), 4.6 mm in internal diameter and 25 cm in length (YMC).

Mobile phase: a mixture of water, acetonitrile and triethylamine (60:40:1) adjusted to pH 7.0 with phosphoric acid.

Flow rate: 1 ml/min.

The bioavailability (BA) was about 23.2% when the water-soluble base, PEG-6000, was used and about 27.9% when the oleaginous base, Witepsol W-35, was used. Thus, high bioavailability values were obtained in both cases. It is, therefore, clear that the composition for rectal administration of the present invention is excellent in absorption kinetics.

The composition for rectal administration based on a water-soluble base is more rapidly absorbed, in terms of the time to maximal plasma concentration (Tmax), than the corresponding composition based on an oleaginous base and, therefore, the former composition is preferred where rapid absorption is required.

EXAMPLE 11

(1) Preparation of a mucosa-adherent matrix

Stearic acid (tetra)glyceride (trade name PS-310; Sakamoto Yakuhin Kogyo Co. ), 1.50 g, was melted at 80° C. After 0.08 g of sodium palmitate was added and evenly melted, 0.4 g of lansoprazole was added and evenly admixed. The mixture was cooled to about 65°–70° C. and 0.02 g of carboxyvinyl polymer (trade name HVW 104; Wako Pure Chemical Industries) was added and evenly dispersed. This dispersion was coated thinly on an aluminum foil spread on a flat surface and allowed to stand at room temperature. The resultant powder was sieved for size selection to provide a matrix ranging from 250–355 µm in particle size.

(2) Preparation of a composition for rectal administration

Witepsol W-35 (Dynamit Nobel), 1.5 g, was evenly melted at about 60° C and then cooled. After cooling to 40° C., 0.5 g of the mucosa-adherent matrix obtained in (1) above (containing 100 mg of lansoprazole) was uniformly dispersed with the temperature being held constant. Then, the matrix was filled, in 0.2 g portions, into rat suppository molds (0.2 g per unit dose, made of brass) warmed to about 40° C. beforehand and allowed to cool to provide a composition for rectal administration.

What we claim is:

1. A composition suitable for providing an anti-ulcer effect and suitable for rectal administration which comprises 2-(2-(3-methyl-4-(2,2,2-trifluoroethoxy)pyridyl) methylsulfinyl)-benzimidazole or a physiologically acceptable salt thereof and a salt of a fatty acid having 6 to 20 carbon atoms in an amount effective to stabilize 2-(2-(3-methyl-4-(2,2,2-trifluoroethoxy)-pyridyl)methylsulfinyl) benzimidazole, said salt and 2-(2-(3-methyl-4-(2,2,2-trifluoroethoxy)pyridyl) methylsulfinyl)-benzimidazole being intermingled in a base suitable for said rectal administration; and wherein said composition comprises about 0.1 to 10 moles of said fatty acid salt per 1 mole of said 2-(2-(3-methyl-4-[2,2,2-trifluoroethoxy)pyridyl) methylsulfinyl)-benzimidazole or said physiologically acceptable salt thereof.

2. The composition according to claim 1, wherein the fatty acid is a saturated fatty acid of 8 to 16 carbon atoms or an unsaturated fatty acid of 12 to 18 carbon atoms.

3. The composition according to claim 1, wherein the salt of the fatty acid of 6 to 20 carbon atoms is an alkali metal or ammonium salt of the fatty acid of 6 to 20 carbon atom.

4. The composition according to claim 3, wherein the alkali metal salt is a sodium salt.

5. The composition according to claim 1, wherein the intermingled mixture of the benzimidazole compound and the fatty acid salt is dispersed in a mucosa-adherent matrix.

6. The composition according to claim 5, wherein the mucosa-adherent matrix comprises a polyglycerin fatty acid ester and a viscogenic agent capable of developing viscosity on contact with water.

7. The composition according to claim 5, wherein the viscogenic agent is an acrylic acid polymer or its salt.

8. A method of treating a gastrointestinal ulcer in a mammal in need thereof, which comprises rectally administering a therapeutically effective dosage of the composition of claim 1 to said mammal.

9. In a composition suitable of the delivery of 2-(2-(3-methyl-4-(2,2,2-trifluoroethoxy)pyridyl) methylsulfinyl)-benzimidazole to a patient to provide an anti-ulcer effect, the improvement which comprises 2-(2-(3-methyl-4-(2,2,2-trifluoroethoxy)pyridyl) methylsulfinyl) benzimidazole or a physiologically acceptable salt thereof in a base suitable for rectal administration, said base including a salt of a fatty acid having 6 to 20 carbon atoms in an amount effective to stabilize 2-(2-(3-methyl-4-(2,2,2-trifluoroethoxy)pyridyl) methylsulfinyl)-benzimidazole, said salt and 2-(2-(3-methyl-4-(2,2,2-trifluoroethoxy)pyridyl) methylsulfinyl] benzimidazole being intermingled in said base; and wherein said composition comprises about 0.1 to 10 moles of said fatty acid salt per 1 mole of said 2-(2-(3-methyl-4-(2,2,2-trifluoroethoxy)pyridyl)methylsulfinyl)-benzimidazole or said physiologically acceptable salt thereof.

* * * * *